(12) United States Patent
Petersen (10) Patent No.: US 9,220,666 B2
(45) Date of Patent: Dec. 29, 2015

(54) SILICON DIOXIDE IN SHAVING PRODUCTS

(71) Applicant: Beiersdorf AG, Hamburg (DE)

(72) Inventor: Miriam Petersen, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 14/382,985

(22) PCT Filed: Feb. 26, 2013

(86) PCT No.: PCT/EP2013/053810
§ 371 (c)(1),
(2) Date: Sep. 4, 2014

(87) PCT Pub. No.: WO2013/131780
PCT Pub. Date: Sep. 12, 2013

(65) Prior Publication Data
US 2015/0037381 A1      Feb. 5, 2015

(30) Foreign Application Priority Data
Mar. 7, 2012   (DE) .......................... 10 2012 203 565

(51) Int. Cl.
| | | |
|---|---|---|
| A61K 8/25 | (2006.01) | |
| A61Q 9/02 | (2006.01) | |
| A61K 8/02 | (2006.01) | |
| A61K 8/37 | (2006.01) | |
| A61K 8/92 | (2006.01) | |
| A61Q 19/00 | (2006.01) | |

(52) U.S. Cl.
CPC ............... *A61K 8/0245* (2013.01); *A61K 8/025* (2013.01); *A61K 8/25* (2013.01); *A61K 8/37* (2013.01); *A61K 8/922* (2013.01); *A61Q 9/02* (2013.01); *A61Q 19/00* (2013.01); *A61K 2800/412* (2013.01)

(58) Field of Classification Search
None
See application file for complete search history.

(56) References Cited

U.S. PATENT DOCUMENTS

| | | |
|---|---|---|
| 5,587,156 A | 12/1996 | Wdowik |
| 5,756,081 A | 5/1998 | Wdowik |
| 6,342,211 B1 | 1/2002 | Ace |
| 6,673,863 B2 | 1/2004 | Travkina et al. |
| 2003/0114572 A1 | 6/2003 | Travkina et al. |
| 2005/0106196 A1 | 5/2005 | Cassin et al. |
| 2007/0031366 A1 | 2/2007 | Meyers et al. |
| 2010/0247914 A1 | 9/2010 | Enomoto et al. |

FOREIGN PATENT DOCUMENTS

| | | |
|---|---|---|
| CA | 2465615 | 5/2003 |
| DE | 10239712 A1 | 3/2004 |
| EP | 0829259 A1 | 3/1998 |
| EP | 1704897 A1 | 9/2006 |
| JP | 10095720 A | 4/1998 |
| JP | 07206640 A | 2/1999 |
| JP | 2003096304 A | 4/2003 |
| WO | 03037287 A1 | 5/2003 |

*Primary Examiner* — H. Sarah Park
(74) *Attorney, Agent, or Firm* — Abel Law Group, LLP (57) ABSTRACT

The invention is a shaving formulation comprising 0.3 to 5% by weight of noncrystalline amorphous silicon dioxide $SiO_2$ which has not been produced pyrogenically, having a particle size of 2 to 30 μm.

18 Claims, 6 Drawing Sheets

SILICON DIOXIDE IN SHAVING PRODUCTS

BACKGROUND OF THE INVENTION

1. Field of the Invention

The invention is a shaving preparation comprising 0.3 to 5% by weight of noncrystalline, amorphous silicon dioxide $SiO_2$, which has not been produced pyrogenically, with a particle size of from 2 to 30 μm.

On account of a reduction in shaving force, the preparation leads to a more skin friendly, more thorough shave.

2. Discussion of Background Information

Shaving beard hair is part of a man's regular hygiene routine. For shaving, almost exclusively special razors were used in the past, the handling of which required some skill to avoid cut injuries and was therefore used predominantly by barbers, whereas nowadays blade razors with one or more blades are used, the handling of which is significantly safer, or electric razors are used.

To obtain a pleasant and thorough shave with the help of a blade razor, one requires, as assistants, water and a shaving product, a shaving preparation.

These shaving preparations are often in the form of foams or gels and are applied to the skin prior to shaving.

The preparations are supposed to prepare the hair for shaving, soften it and produce a gliding film which permits problem-free gliding of the blade over the skin.

A classic shaving product is shaving soap which is lathered using a brush and spread in the shaving zone. More recent products are shaving foams and self-foaming shaving gels.

The constructions of modern blade razors virtually exclude serious cut injuries. Nevertheless, irritations of the skin can arise if the blade does not glide in an optimal manner over the skin. Similarly, microcuts can occur on areas of uneven skin, particularly in the perifolicular region, aided by pulling or bending processes at the hair to be shaved. The desire for the most thorough shave possible, i.e. a cut as close to the skin as possible and an exclusion of irritations, i.e. a distance from blade to the skin, can only be combined with difficulty.

The key for the most optimum shave possible is the shaving product. Shaving products soften the hair, which makes the cutting operation easier and thus leads to less pressure on the hair and thus to fewer pulls. Known shaving products, foams and gels are based on basic preparations since, as is known, the soap-based and thus alkaline preparations lead to a swelling of the hair, and consequently a more thorough shave can take place.

At the same time, the shaving preparations form a lubricant film which reduces the friction and thus allows the blade to gently glide over the skin. Investigations show, however, also that hair that is too soft yields to the blade pressure and moves to one side as a result of bending, which shifts the cutting plane from horizontal into the vertical direction, and thus leads to frayed cutting edges, which is detrimental to the thoroughness. Something similar is observed if the gliding effect on the hair is also too great. The blade slips on the hair, does not find a holding point for a smooth cut, which often leads to a pulling out of the hair, and thus to an unpleasant sensation, and, as a result of these frayed ends, leads to an untidy, not very thorough shave.

Shaving auxiliaries are occasionally added to the known shaving preparations. These are particulate compounds or water-soluble polymers, such as PEG-14M, PEG-7M, PEG-90M (=PEG 90000), PEG 45M (polymers of ethylene oxide with average degrees of polymerization as numbered multiplied by factor 1000), acrylates, PTFE (polytetrafluoroethylene) or cellulose derivatives which are suitable for improving the glidability.

U.S. Pat. No. 6,342,211 B1 describes the process of the shaver slipping on the hair and the subsequent not very thorough shaving result. To solve this problem, 0.02-0.5% polyacrylamide suspended in water with a high molecular weight of MW=14 million is used in a shaving product which, according to the principle of a ball-bearing, brings about an optimum gliding effect of the shaver on the skin, but not on the hair.

U.S. Pat. No. 5,756,081 and U.S. Pat. No. 5,587,156 describe shaving preparations which comprise solid, insoluble, particulate additives (e.g. PTFE, PE, nylon, silica etc.), which offer the blade physical assistance, as a result of which cuts are prevented and the skin feel after shaving is improved.

EP 829 259 A1 describes shaving products which comprise microparticles (e.g. PA, kaolin, PTFE, PV, $SiO_2$ etc.). These microparticles serve as exfoliating particles for removing dead skin cells. Silicon dioxide particles here can have a particle size of from 7 to 14 microns.

EP 1 439 816 B1 describes pyrogenically produced silicon dioxide in cosmetic preparations, where the $SiO_2$ granules act as a carrier for cosmetic active ingredients and/or auxiliaries.

US 2007 0031366 A2 describes a process for achieving a more thorough shave. For this, the skin is treated inter alia with a pre-shave preparation which comprises skin-exfoliating particles such as silica, metal oxides, PE etc.

EP 1 704 897 B1 describes post-foaming shaving products consisting of water, C10-C24-alkanecarboxylic acid, neutralizing agent, nonionic surfactant, hydrophobic coemulsifier, C3-C9 polyol, thickening polymer, which is not PEG, PEG with an average molecular weight of at least 300 000 daltons and silica. By reducing the content of high molecular weight PEGs, as well as by adding silica together with a specific combination of soaps, nonionic surfactants, hydrophobic coemulsifiers, polyols and polymer thickeners, the aim is to improve the application properties, the skin feel, the foaming properties, and also the production and filling properties.

It is desirable to achieve a thorough shave with the lowest possible, or even better no, irritations of the skin.

In this connection, a cut of the hair as close to the skin as possible should be achieved, where the slipping of the razor blade on the hair is to be avoided and therefore fewer vertical cuts take place, meaning that the hair has fewer frayed ends.

SUMMARY OF THE INVENTION

The invention is a shaving preparation with at least one oil phase which comprises noncrystalline, amorphous silicon dioxide $SiO_2$, which has not been produced by pyrogenic means, having a particle size of from 2 to 30 μm.

The weight fraction of the non-pyrogenically produced silicon dioxide is 0.3 to 5% by weight, based on the total mass of the preparation, preferably 0.4 to 1.2% by weight.

The fraction of silicon dioxide, based on the total mass of the preparation with propellant, is preferably 0.4 to 1% by weight. The fraction of silicon dioxide based on the total mass of the preparation without propellant is preferably 0.5 to 1.2% by weight.

It has surprisingly been found that shaving products which comprise the silicon dioxide according to the invention having this particle size do not exhibit the disadvantage of the prior art.

On account of the $SiO_2$ present in the oil phase, the shaving preparation according to the invention forms a particulate gliding layer and permits an optimally thorough shave without skin irritations. Similarly to a ball-bearing principle, the $SiO_2$ particles according to the invention permit the blade to glide on the skin. In contrast to the fillers known from the prior art, these particles are unable to form a gliding layer on the skin for geometric reasons and the blade finds immediate hold for a thorough cut.

Shaving means are dry or wet shaving apparatuses, metal blades or knives.

In order to be able to make a statement concerning the shaving thoroughness and also suitability of a shaving product, the shaving force can be determined.

The shaving force is a combination of cutting and gliding processes. The shaving product is applied to a prepared pig skin and then the shaver (the shaving means), which is attached to an adapter and linked to a standard testing machine, is drawn over the pig skin. In so doing, the (beard) hair is cut and the force required for this is recorded (first shaving force). This operation is then repeated (second shaving force). The pig skin is then thoroughly freed from any remaining stubble using a separate razor and product is applied again. The razor now glides over the smooth skin, from which conclusions as the gliding properties of the product can be drawn (gliding force).

A cosmetic preparation, a shaving preparation, is here able to influence the gliding and cutting forces.

BRIEF DESCRIPTION OF THE DRAWINGS

In the accompanying drawings.

DETAILED DESCRIPTION OF THE INVENTION

In an in-vitro shaving force measurement on pig skin, 3 shaving products were compared with one another. All three preparations comprise 0.5% by weight of a polymer or of a particle (nylon-12, silicon dioxide (Silica Pearl P-4), polyethylene (Micropoly 1160S)).

The test products are listed in Table 1 below.

TABLE 1

| INCI | Test product 1 (10) m [%] | Test product 2 (20) m [%] | Test product 3 (30) m [%] |
|---|---|---|---|
| Stearic acid | 5.50 | 5.50 | 5.50 |
| Propylene glycol | 1.00 | 1.00 | 1.00 |
| Aqua | ad 100 | ad 100 | ad 100 |
| *Persea Gratissima* Oil | 0.10 | 0.10 | 0.10 |
| Laureth-23 | 2.75 | 2.75 | 2.75 |
| Nylon-12 | 0.50 | | |
| SILICA PEARL P-4 | | | 0.50 |

TABLE 1-continued

| INCI | Test product 1 (10) m [%] | Test product 2 (20) m [%] | Test product 3 (30) m [%] |
|---|---|---|---|
| MICROPOLY 1160S | | 0.50 | |
| Glycerin | 2.48 | 2.48 | 2.48 |
| Potassium hydroxide | 0.17 | 0.17 | 0.17 |
| Hydroxypropyl Methylcellulose | 0.15 | 0.15 | 0.15 |
| *Gossypium Herbaceum* Seed Oil | 0.40 | 0.40 | 0.40 |
| Coco-Caprylate/Caprate | 0.50 | 0.50 | 0.50 |
| Piroctone Olamine | 0.10 | 0.10 | 0.10 |
| Triethanolamine | 2.79 | 2.79 | 2.79 |
| PEG-7M | 0.05 | 0.05 | 0.05 |
| Bisabolol | 0.20 | 0.20 | 0.20 |
| Perfume | 0.30 | 0.30 | 0.30 |

The preparation is then admixed with propellant gas:

| | | | |
|---|---|---|---|
| Isobutane | 2.88 | 2.88 | 2.88 |
| Propane | 0.92 | 0.92 | 0.92 |
| Butane | 0.20 | 0.20 | 0.20 |

Test product 05 is pure water.

Figure 1:
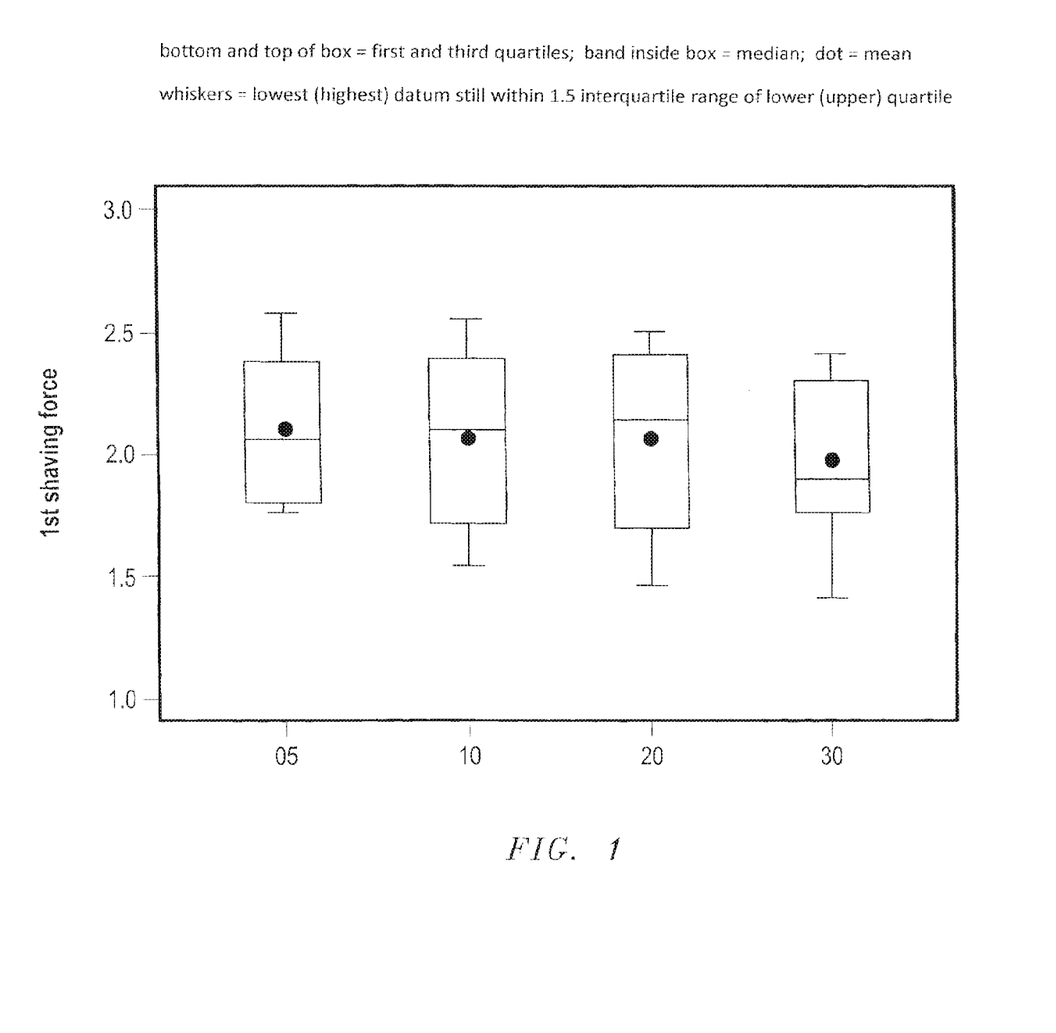
FIGS. 1 and 2 graphically represent the first and second shaving forces obtained with three tested products and pure water in the in-vitro shaving force measurement with pig skin described below.
Figure 2:
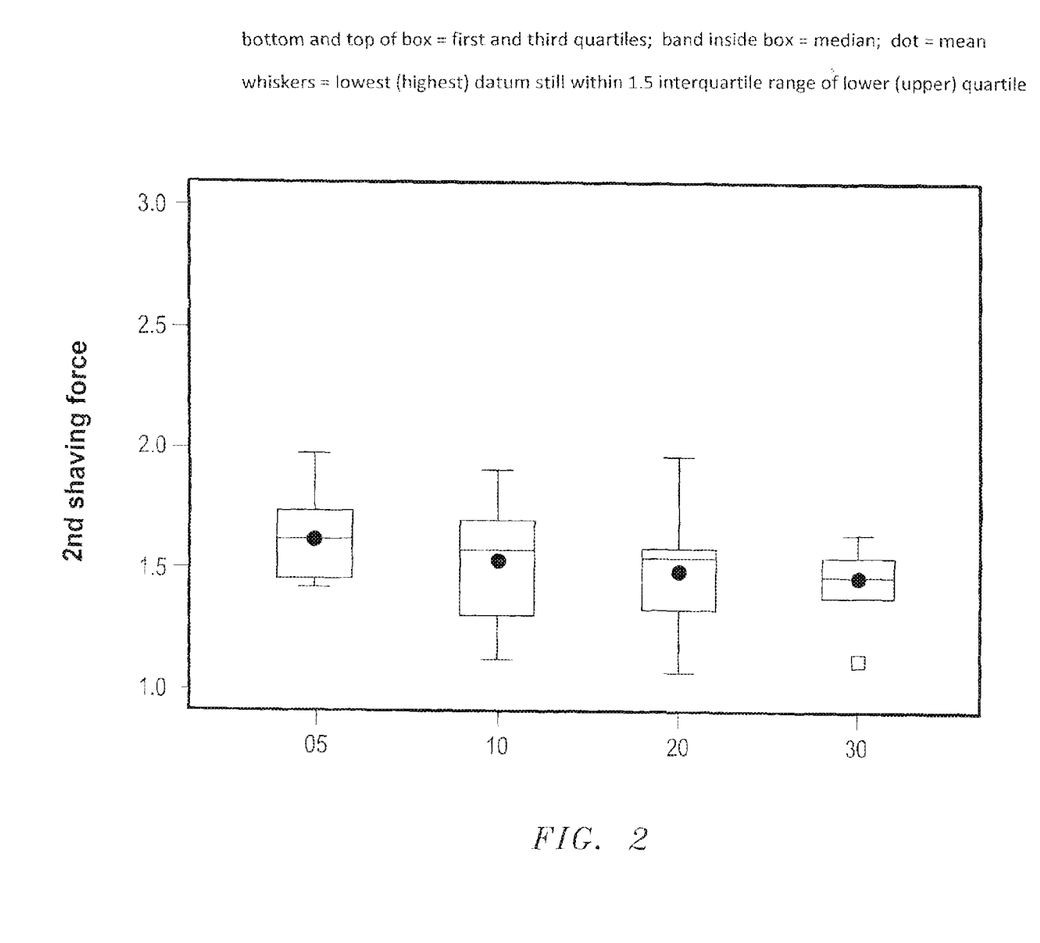
Figure 3:
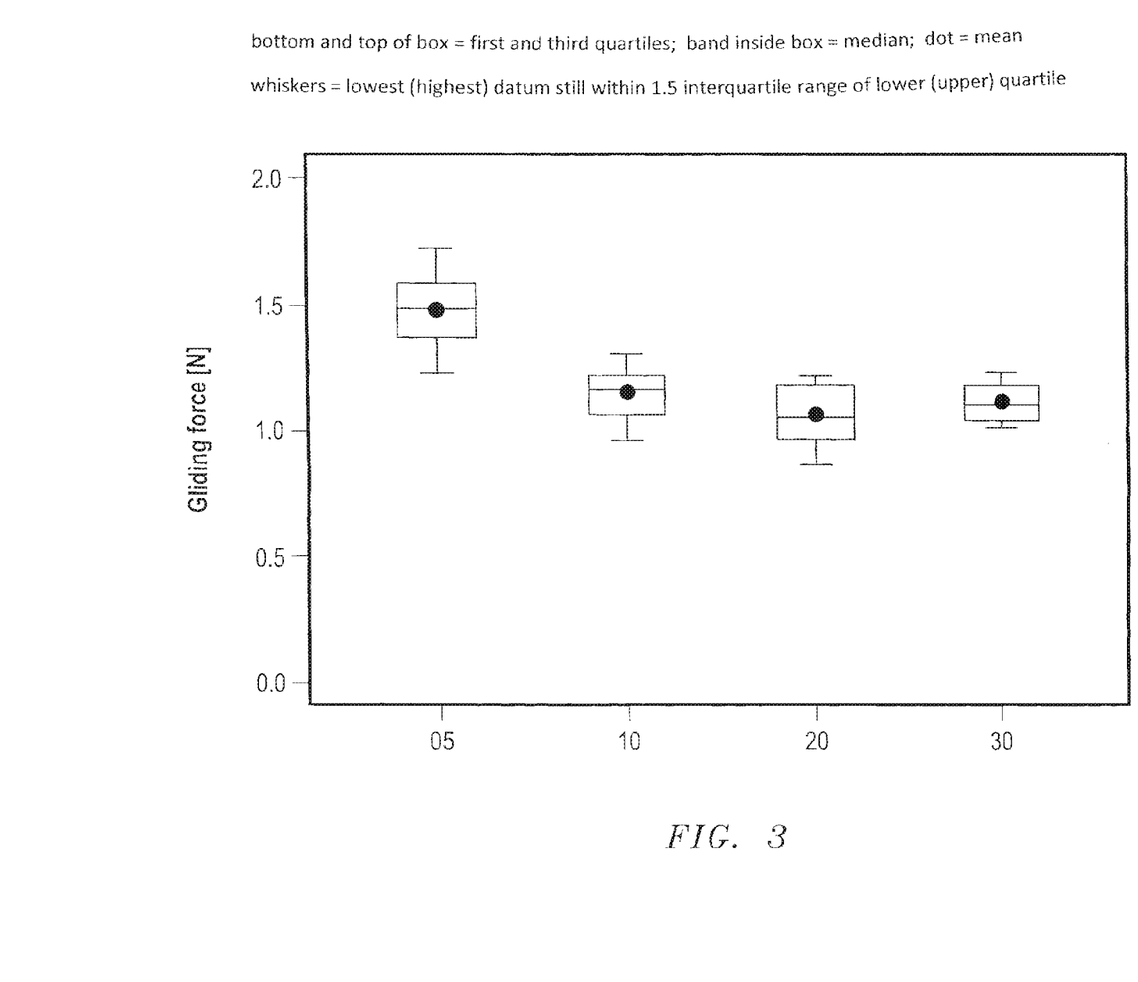
FIG. 3 graphically represents the gliding force obtained with three tested products and pure water in the in-vitro gliding force measurement with pig skin described below.

FIGS. 1 and 2 show the first and second shaving forces and FIG. 3 shows the gliding forces of the test products. The table below illustrates the measurement results.

TABLE 2

Shaving and gliding force; inductive statistics

| Parameter | Comparison | Adjusted p | Raw p | Result |
|---|---|---|---|---|
| Shaving force - 1st stroke | 05-10 | 0.9069 | 0.5087 | n.s. |
| | 05-20 | 0.9104 | 0.5146 | n.s. |
| | 05 > 30 | 0.1929 | 0.0499 | l.s. |
| | 10-20 | 1.0000 | 0.9926 | n.s. |
| | 10-30 | 0.5109 | 0.1738 | n.s. |
| | 20-30 | 0.5051 | 0.1711 | n.s. |
| Shaving force - 2nd stroke | 05-10 | 0.4067 | 0.1263 | n.s. |
| | 05-20 | 0.2029 | 0.0531 | n.s. |
| | 05 > 30 | 0.0555 | 0.0122 | l.s. |
| | 10-20 | 0.9674 | 0.6518 | n.s. |
| | 10-30 | 0.6641 | 0.2630 | n.s. |
| | 20-30 | 0.8998 | 0.4962 | n.s. |
| Gliding force | 05 > 10 | <.0001 | <.0001 | m.s. |
| | 05 > 20 | <.0001 | <.0001 | m.s. |
| | 05 > 30 | <.0001 | <.0001 | m.s. |
| | 10-20 | 0.4453 | 0.1431 | n.s. |
| | 10-30 | 0.8920 | 0.4847 | n.s. |
| | 20-30 | 0.8499 | 0.4271 | n.s. |

Table 2: Comparison among treatments (ANOVA—generalized Tukey's test, averaged data)

Surprisingly, it is found that silicon dioxide according to the invention (Silica Pearl P-4) reduces the shaving force compared to water significantly and compared to polyethylene and nylon-12 descriptively. In the gliding properties, all 3 products turn out significantly better than water, with there being no significant differences between the products.

The silicon dioxide according to the invention forms a particulate gliding layer in the shaving preparation on the skin which, similarly to the ball-bearing principle, permits a gliding of the blade on the skin. However, since the silicon dioxide particles are unable to form a gliding layer on the hair on account of their geometrically very round shape, the blade finds an immediate hold for an optimum cut. Consequently, the required cutting forces are lower and the shave is thus more pleasant. Silicon dioxide according to the invention thus has a positive influence of the shaving forces in the shaving process.

The preparation according to the invention can thus be used for reducing the shaving force following topical application of the preparation.

In an in-vivo panel test, in which trained subjects shave according to a standardized procedure, a shaving product with silicon dioxide according to the invention was compared against a shaving product containing nylon-12. The preparation with silicon dioxide according to the invention has significantly higher cushioning.

The parameter of cushioning is defined as the amount of product which is detectable between blade and skin, i.e. cushions the razor before contact with the skin. The higher the cushioning, the more product there is between blade and skin, and the higher the shaving comfort.

Furthermore, it is observed that the preparation according to the invention advantageously leaves behind a significantly higher film on the skin.

Numerically, after shaving, the gliding of the finger over the skin is higher for wet skin. The scraping of the blade (noise) is numerically lower.

Surprisingly, the cushioning with preparation according to the invention is higher, although the $SiO_2$ particles with an average 10 μm particle size are only half as large as the nylon-12 particles with an average 20 μm. One would thus expect a lower cushioning for the smaller particles since with smaller particles the distance between the blade and the skin is less.

The following preparations in Table 3 were analyzed in the in vivo test:

TABLE 3

In vivo panel test - cushioning

| INCI | Test product 1 m [%] | Test product 2 m [%] |
|---|---|---|
| Stearic Acid | 5.50 | 5.50 |
| Propylene Glycol | 1.00 | 1.00 |
| Aqua | ad 100 | ad 100 |
| *Persea Gratissima* Oil | 0.10 | 0.10 |
| Laureth-23 | 2.75 | 2.75 |
| Nylon-12 | 0.50 | |
| Silicon dioxide | | 0.50 |
| Glycerin | 2.48 | 2.48 |
| Potassium hydroxide | 0.17 | 0.17 |
| Hydroxypropyl Methylcellulose | 0.15 | 0.15 |
| *Gossypium Herbaceum* Seed Oil | 0.40 | 0.40 |
| Coco-Caprylate/Caprate | 0.50 | 0.50 |
| Piroctone Olamine | 0.10 | 0.10 |
| Triethanolamine | 2.79 | 2.79 |
| PEG-7M | 0.05 | 0.05 |
| Bisabolol | 0.20 | 0.20 |
| Perfume | 0.30 | 0.30 |

The preparation is then admixed with propellant:

| | | |
|---|---|---|
| Propane | 0.92 | 0.92 |
| Butane | 0.20 | 0.20 |
| Isobutane | 2.88 | 2.88 |

The assessment was carried out by trained subjects. The assessment is carried out by reference to a scale from 0 to 10 in steps of 0.5. For each attribute, a standard value is defined. The higher the value, the more marked the attribute.

Table 4 below shows the test results of the cushioning investigation compared also to a market product.

TABLE 4

In vivo panel test results

| | Average value Test product 1 0.5% nylon 12 | Average value Test product 2 0.5% silica pearl P4 (SiO2) | Standard values Nivea Sensitive shaving foam | Significance (>95%) | Significance (>90%) |
|---|---|---|---|---|---|
| On the watch glass | | | | | |
| Dimensional stability | 7.8 | 7.7 | 8 | | |
| Rigidity | 5.0 | 5.1 | 5 | | |
| On the face | | | | | |
| Spreadability | 7.0 | 6.9 | 7 | | |
| Uniformity | 7.8 | 7.9 | 8 | | |
| Cooling effect | 1.0 | 1.1 | 1 | | |
| Thread drawing | 1.1 | 1.0 | 1 | | |
| Stickiness | 5.0 | 4.7 | 5 | | |
| Peak formation | 4.8 | 4.9 | 5 | | |
| During shaving | | | | | |
| Gliding | 6.0 | 6.0 | 6 | | |
| Cushioning | 6.0 | 6.3 | 6 | ++ | |
| Blade scraping | 3.5 | 3.4 | 3.5 | | |
| Rinseability | 7.9 | 7.6 | 8 | | |
| After shaving - wet | | | | | |
| Skin gliding | 5.9 | 6.2 | 6 | | |
| Film on the skin | 1.7 | 2.1 | 2 | | + |
| After shaving - dry | | | | | |
| Stubble | 1.9 | 1.9 | 2 | | |
| Skin tautness | 1.5 | 1.4 | 1.5 | | |
| Cooling effect | 1.2 | 1.2 | 1 | | |
| Suppleness | 5.9 | 5.9 | 6 | | |

Figure 4:
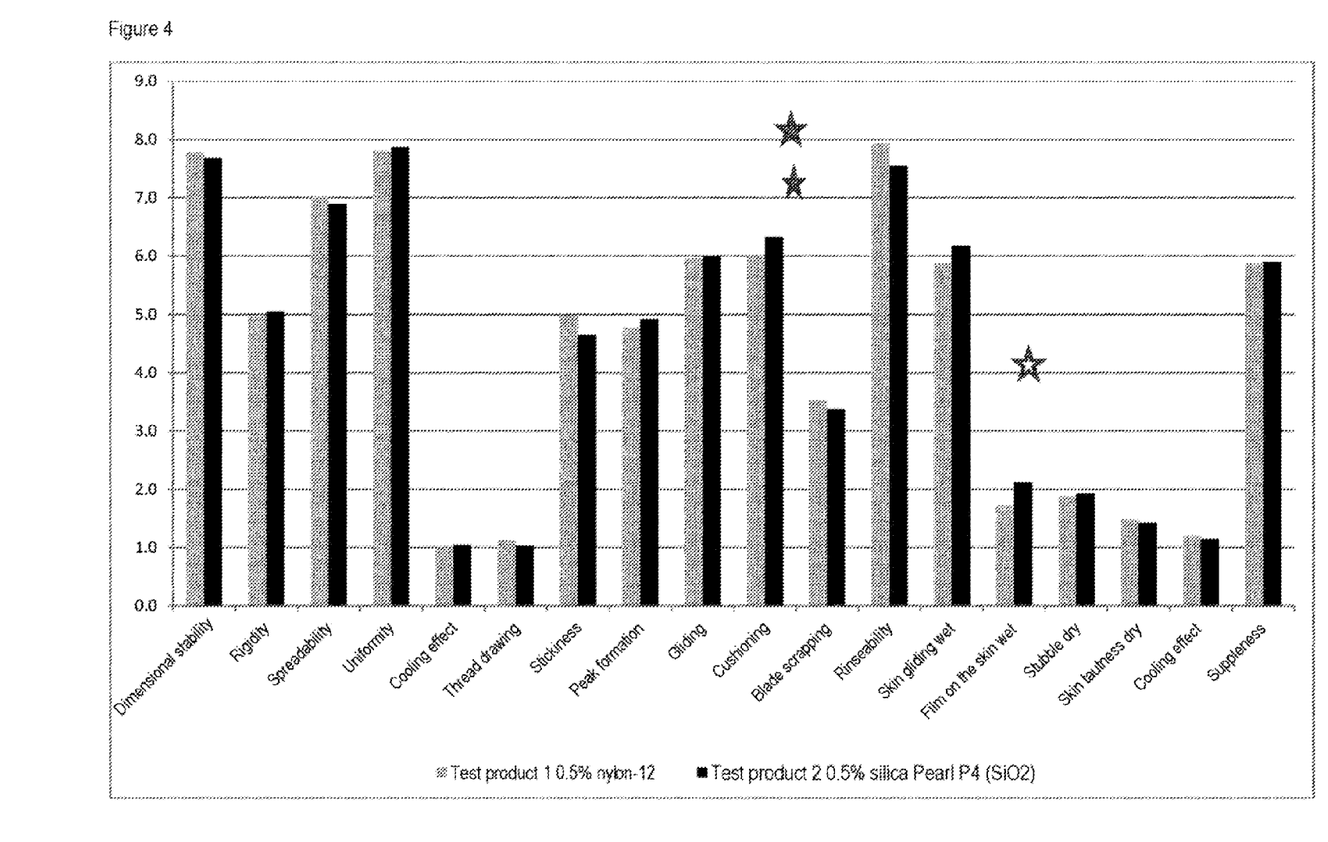
FIG. 4 graphically represents the test panel results set forth in Table 4 below with respect to a cushioning test with a product of the invention and a commercial product.

The results of the panel test are shown in FIG. 4.

In a home-in-use test with 100 male consumers, 2 shaving products with 0.5% by weight silicon dioxide according to the invention and 0.5% by weight nylon-12 were tested against a standard commercial shaving product without particulate additives. The preparation according to the invention turned out significantly better in the parameters: "skin feels soft and supple" and "shaving was thorough" as well as in the overall assessment. Numerically, the preparation according to the invention with silicon dioxide was moreover better in "foam can be spread easily on the skin", "foam adheres well on the face", "skin is not taut", "beard hair is prepared optimally for shaving".

The fact that the preparations with silicon dioxide according to the invention are considerably better in respect of thoroughness can be attributed to the so-called "ball-bearing principle". This in turn is based on the particle size according to the invention of the selected silicon dioxide particles. Since no particulate gliding layer is formed on the hair on account of the particular geometric shape of the SiO2 particles according to the invention, the blade then finds an immediate hold on the hair. Consequently, the hair is cut clean without frayed ends, which would be detrimental to the thoroughness.

The preparations known in the prior art (e.g. U.S. Pat. No. 6,342,211 B1) comprise very large polyacrylamide molecules, present in suspended form in water, which achieve only a lubrication of the skin, but not of the hair.

Surprisingly, the preparations according to the invention exhibit the same effect, although, by contrast, the $SiO_2$ particles are very small solid particles with an average size of in particular advantageously 5-10 µm. This is surprising with the current knowledge relating to shaving and gliding property of shaving means and products.

A further decisive difference is that, according to the invention, the $SiO_2$ particles are present in the oil phase. If the particles are present in the oil phase, which corresponds in the case of a O/W emulsion preparation to the inner, discontinuous phase, an influence on the hair, for example the "lubrication" of the hair, is less probable than if the particles were to be present in the water phase. The supporting gliding effect for the blade of the shaving means, however, is nevertheless present and leads to the advantageous properties.

One advantage here is that the $SiO_2$ particles can be incorporated more easily into the oil phase.

Furthermore, it was shown in vitro and in vivo that for example customary particles made of PE or nylon-12 do not have the same positive effect as silicon dioxide according to the invention. Similarly, the particles listed in the prior art with a particle size of 50-200 µm are considerably larger than silicon dioxide according to the invention.

It is known in this connection that particles above a size of more than 40 µm can be felt as exfoliation particles on the skin. Accordingly, such large particles in a shaving product must be rather unpleasant during use. The thoroughness is also significantly reduced since the distance between the blade and the skin is very greatly enlarged as a result of the particle size.

Silicon dioxide is a generic term for the modifications of the oxides of silicon with the empirical formula $SiO_2$. In the German language, the term Kieselsäure [silica] is sometimes used incorrectly for silicon dioxide. According to the invention, silicon dioxide is understood not to be silica or precipitated silica as mentioned in the prior art.

Synthetic $SiO_2$, which is present in amorphous form, is generated industrially in large amounts in various processes.

One production variant is the generation of so-called pyrogenic $SiO_2$ in an oxyhydrogen flame, starting from liquid chlorosilane such as silicon tetrachloride ($SiCl_4$).

During the production of pyrogenic $SiO_2$, relatively large agglomerates can form during cooling which have more of a chain-like structure. I.e. during the pyrogenic production of silicon dioxide, the spherical shape of the silicon dioxide preferred according to the invention is not ensured. According to the invention, therefore, these forms of silicon dioxide, pyrogenic $SiO_2$, are excluded.

The silicon dioxide according to the invention is rather noncrystalline, amorphous silicon dioxide $SiO_2$, which is not produced pyrogenically.

Figure 5:
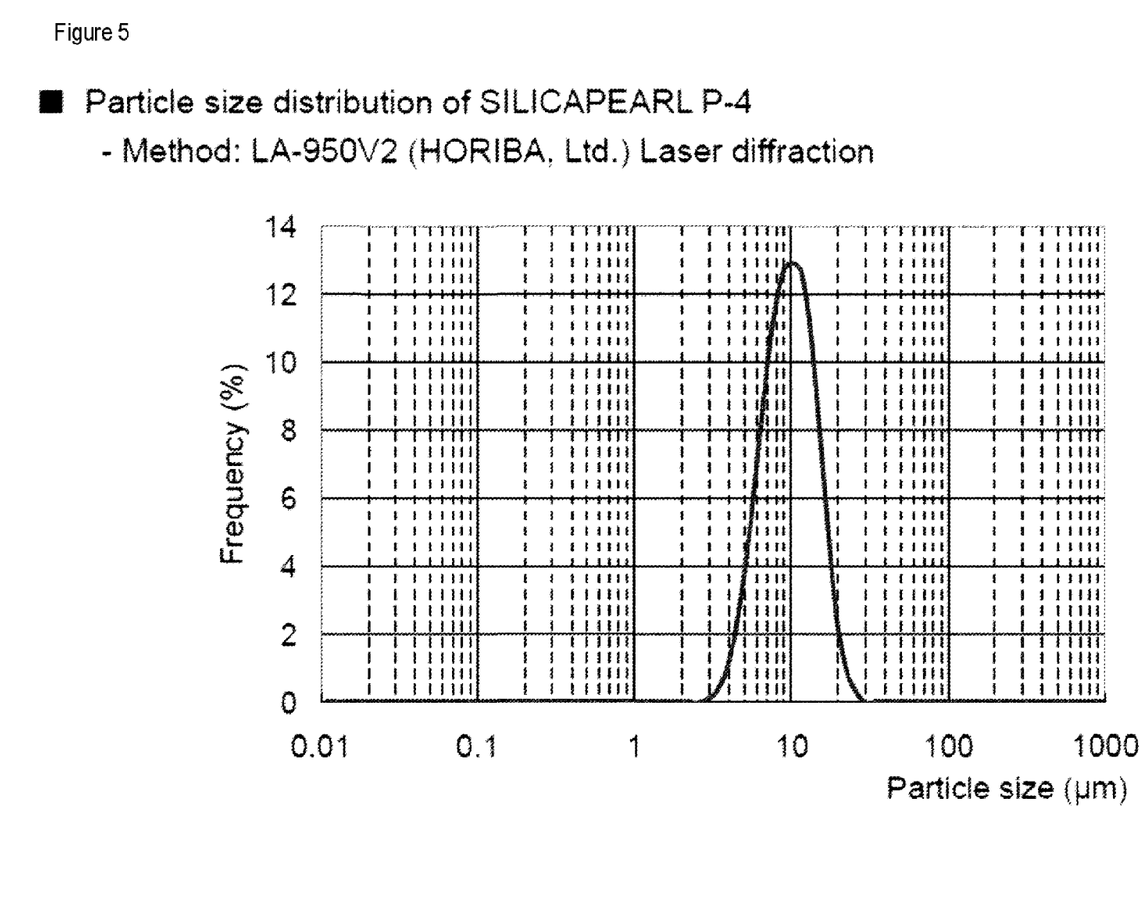
FIG. 5 is a graph showing the particle size distribution of a silicon dioxide product which is suitable for use in the instant invention.

A further particular property of the $SiO_2$ particles according to the invention lies in the narrow particle size distribution, as is shown in FIG. 5.

The $SiO_2$ according to the invention has a particle size of from 2 to 30 µm, in particular 5 to 15 µm, in particular in the range around 10 µm. The range around 10 µm is to be understood as meaning the range from 9.0 to 12.0 µm, advantageously as the range from 9.5 to 11.0 µm.

The raw material Silica Pearl P-4 from JGC, for example, can be used as $SiO_2$ according to the invention.

Figure 6:
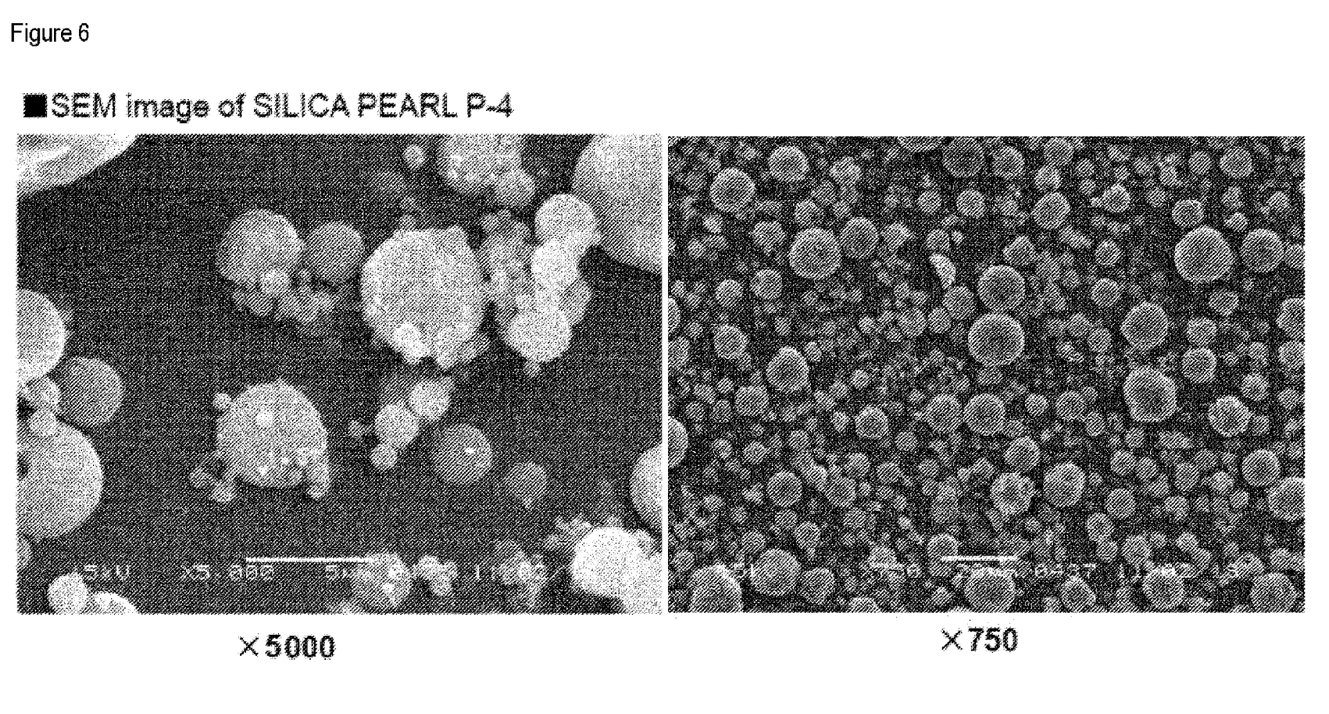
FIG. 6 shows SEM images of a silicon dioxide product which is suitable for use in the instant invention.

Further characteristics of the $SiO_2$ particles according to the invention lie in their round geometric shape, as is shown in FIG. 6.

Many different techniques have been developed for determining the particle size distribution, but laser scattering is the preferred method in many different sectors of industry.

The laser scattering or LALLS (Low Angle Laser Light Scattering) method can be used for the destruction-free analysis of wet and dry samples of particles with a size of from 0.02 to 2000 micrometers and has particular advantages which positively differentiate it from other methods in the case of many materials.

The definition of the term "particle size distribution" is to be understood as follows. Particles are three-dimensional structures. Three parameters (length, width, height) are required in order to be able to give a complete description of particles. It is thus difficult to describe a particle by stating a single number which corresponds to the particle size. In the majority of the methods for determining size, it is therefore assumed that the material to be measured is spherical since a sphere is the only shape which can be described by means of a single number (the diameter).

If the product consists of spherical particles, then the particle size is clearly defined by stating the sphere diameter, as according to the invention preferably in the range from 5 to 15 µm. However, the majority of the finely particulate materials do not consist of spheres, but of more or less irregularly shaped particles which, in an extreme case, can be needle-like, and in another platelet-like. The dispersity property of the individual particles can be described here by the particle volume and additional parameters such as sphericity (sphere similarity). Instead of the single-parameter function for spheres, a multiparameter dispersity function is obtained, the determination of which is associated with great measurement complexity. Such complexity is only justified if it serves to provide essential information about product properties.

Consequently, one normally limits oneself in practice and also in accordance with the invention to stating a single-parameter distribution function for the particle size.

The preparations according to the invention are preferably emulsion-based preparations, gels, foams or creams. The preparations according to the invention can also be provided as lotion, spray or aerosol.

The accompanying substance required in each case for this purpose, such as propellant gases in the case of aerosols, can be chosen by the person skilled in the art from the known agents.

Emulsions are advantageous and comprise e.g. fats, oils, waxes and other fatty bodies, as well as water and an emulsifier, as is customarily used for such a type of formulation.

The preparations according to the invention are advantageously shaving foams, shaving gels or shaving creams.

Preparation according to the invention comprises an oil or lipid phase.

The lipid phase can advantageously be selected from the following substance group:
  mineral oils, mineral waxes
  oils, such as triglycerides of capric acid or of caprylic acid, also natural oils such as e.g. castor oil;
  fats, waxes and other natural and synthetic fatty bodies, preferably esters of fatty acids with alcohols of low carbon number, e.g. with isopropyl, propylene glycol or glycerol, or esters of fatty alcohols with alkanoic acids of low carbon number or with fatty acids;
  alkyl benzoates;
  silicone oils such as dimethylpolysiloxanes, diethylpolysiloxanes, diphenylpolysiloxanes, and mixed forms thereof.

The oil phase of the preparation, oleogels or hydrodispersions or lipodispersions in the context of the present invention are advantageously selected from the group of the esters of saturated and/or unsaturated, branched and/or unbranched alkanecarboxylic acids of chain length from 3 to 30 C atoms and saturated and/or unsaturated, branched and/or unbranched alcohols of chain length from 3 to 30 C atoms, from the group of the esters of aromatic carboxylic acids and saturated and/or unsaturated, branched and/or unbranched alcohols of chain length from 3 to 30 C atoms. Such ester oils can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and also synthetic, semisynthetic and natural mixtures of such esters, e.g. jojoba oil.

The oil phase can also advantageously be selected from the group of the branched and unbranched hydrocarbons and hydrocarbon waxes, the silicon oils, the dialkyl ethers, the group of the saturated or unsaturated, branched or unbranched alcohols, and also the fatty acid triglycerides, namely the triglycerol esters of saturated and/or unsaturated, branched and/or unbranched alkane carboxylic acids of chain length from 8 to 24, in particular 12-18 C atoms. The fatty acid triglycerides can for example be advantageously selected from the group of synthetic, semisynthetic and natural oils, e.g. olive oil, sunflower oil, soya oil, peanut oil, rapeseed oil, almond oil, palm oil, coconut oil, palm kernel oil and the like.

Any desired mixtures of such oil and wax components are also to be used advantageously in the context of the present invention. It may also optionally be advantageous to use waxes, for example cetyl palmitate, as the sole lipid component of the oil phase.

The oil phase advantageously comprises one or more lipids selected from Persea Gratissima oil, Gossypium Herbaceum seed oil, coco-caprylate/caprate and/or isopropyl palmitate.

The compositions according to the invention can also optionally comprise additives customary in cosmetics, for example perfume, thickeners, deodorants, antimicrobial substances, refatting agents, complexing and sequestering agents, pearlizing agent, plants extracts, vitamins, active ingredients, preservatives, bactericides, dyes, pigments which have a coloring effect, thickening agents, moisturizing and/or humectant substances, fats, oils, waxes, if not excluded, or other customary constituents of a cosmetic or dermatological formulation such as alcohols, polyols, polymers, foam stabilizers, electrolytes, organic solvents or silicone derivatives.

Moisturizers can advantageously also be used as anti-wrinkle active ingredients to protect against skin changes as occur e.g. during skin aging.

Preparations according to the invention are produced in accordance with customary manufacturing instructions. The $SiO_2$ particles are incorporated for example with the input of energy using an Ultraturrax (laboratory scale) or by means of a heavy stirrer in the tank (production) into the fatty phase of the preparation. $SiO_2$ particles are not water-soluble, and therefore a dispersion in the oil phase is advantageous.

The examples below illustrate the preparations according to the invention. The data refer to parts by weight, based on the total mass of the particular preparation with or without propellant.

Example Shaving Foams

| INCI | Ex. 1 m [%] | Ex. 2 m [%] |
|---|---|---|
| Stearic acid | 5.50 | 5.50 |
| Propylene glycol | 1.00 | |
| Aqua | ad 100 | ad 100 |
| Persea Gratissima Oil | 0.10 | |
| Laureth-23 | 2.75 | 2.75 |
| Silicon dioxide* | 0.50 | 0.50 |
| Glycerin | 2.48 | 2.60 |
| Potassium hydroxide | 0.17 | 0.17 |
| Hydroxypropyl Methylcellulose | 0.15 | 0.15 |
| Gossypium Herbaceum Seed Oil | 0.40 | |
| Coco-Caprylate/Caprate | 0.50 | 0.50 |
| Piroctone Olamine | 0.10 | 0.10 |
| Triethanolamine | 2.79 | 2.79 |
| PEG-7M | 0.05 | 0.05 |
| Bisabolol | 0.20 | |
| Maltodextrin + Chamomilla Recutita Flower Extract | | 0.01 |
| Perfume | 0.30 | 0.30 |

96% by weight of the above preparation, based on the total mass with propellant, is admixed with propellant as follows:

| Isobutane | 2.88 | 2.88 |
|---|---|---|
| Propane | 0.92 | 0.92 |
| Butane | 0.20 | 0.20 |

Example Shaving Gels

| INCI | Ex. 3 m [%] | Ex. 4 m [%] |
|---|---|---|
| Isopropyl Palmitate | | 1.50 |
| Propylene glycol | 0.50 | |
| Aqua | ad 100 | ad 100 |
| Tocopheryl Acetate | | 0.01 |
| Paraffinum Liquidum | 1.50 | |
| BHT | 0.03 | 0.03 |
| Polyisobutene | 0.50 | 0.50 |
| Silicone dioxide* | 0.50 | 0.50 |
| Glycerin | 2.48 | 2.48 |
| Hydroxyethylcellulose | 0.40 | 0.40 |
| Hydroxypropyl Methylcellulose | 0.10 | 0.10 |
| Palmitic Acid | 8.40 | 8.40 |
| Oleth-20 | 6.00 | 6.00 |
| PEG-14M | 0.10 | 0.10 |
| Gossypium Herbaceum Seed Oil | 0.50 | |
| Piroctone Olamine | 0.10 | 0.10 |
| PEG-90 Glyceryl Isostearate | 0.35 | 0.35 |
| Laureth-2 | 0.04 | 0.04 |
| Triethanolamine | 6.00 | 6.00 |
| Bisabolol | 0.20 | |
| Perfume | 0.40 | 0.20 |
| Maltodextrin + Chamomilla Recutita Flower Extract | | 0.01 |

*Non-crystalline, amorphous silicon dioxide $SiO_2$, not produced pyrogenically.

95% by weight of the above preparation, based on the total mass with propellant, is admixed with propellant as follows:

| Isopentane | 3.75 | 3.75 |
|---|---|---|
| Isobutane | 1.25 | 1.25 |

What is claimed is:

1. A shaving preparation, wherein the preparation comprises at least one oil phase and from 0.4% to 1.2% by weight, based on a total mass of the preparation, of particles of non-crystalline, amorphous silicon dioxide $SiO_2$ which has not been produced pyrogenically, the particles having a particle size of from 5 μm to 15 μm and a round shape.

2. The preparation of claim 1, wherein the particles have a particle size of around 10 μm.

3. The preparation of claim 1, wherein the at least one oil phase comprises one or more lipids selected from Persea Gratissima oil, Gossypium Herbaceum seed oil, coco-caprylate/caprate, isopropyl palmitate.

4. The preparation of claim 1, wherein the preparation further comprises a propellant.

5. The preparation of claim 4, wherein the propellant comprises one or more of propane, butane, isobutane, isopentane.

6. The preparation of claim 1, wherein the preparation is present as an emulsion-based preparation.

7. The preparation of claim 1, wherein the preparation is present as a gel, a foam and/or a cream.

8. The preparation of claim 1, wherein the preparation is present as a lotion, spray or aerosol.

9. The preparation of claim 1, wherein the preparation further comprises a thickener.

10. A method of reducing the shaving force provided by a topically applied shaving preparation that comprises at least one oil phase, wherein the method comprises including in the shaving preparation from 0.4% to 1.2% by weight, based on a total mass of the preparation, of particles of noncrystalline, amorphous silicon dioxide $SiO_2$ which has not been produced pyrogenically, the particles having a particle size of from 5 μm to 15 μm and a round shape.

11. The method of claim 10, wherein the at least one oil phase comprises one or more lipids selected from Persea Gratissima oil, Gossypium Herbaceum seed oil, coco-caprylate/caprate, isopropyl palmitate.

12. The method of claim 10, wherein the preparation further comprises a propellant.

13. The method of claim 12, wherein the propellant comprises one or more of propane, butane, isobutane, isopentane.

14. The method of claim 10, wherein the preparation is present as an emulsion-based preparation.

15. The method of claim 10, wherein the preparation is present as a gel, a foam and/or a cream.

16. The method of claim 10, wherein the preparation is present as a lotion, spray or aerosol.

17. The method of claim 10, wherein the preparation further comprises a thickener.

18. The method of claim 10, wherein the particles have a particle size of around 10 μm.

\* \* \* \* \*